(12) United States Patent
Vielhaber

(10) Patent No.: US 10,857,085 B2
(45) Date of Patent: Dec. 8, 2020

(54) PREPARATIONS COMPRISING CARNOSINES

(71) Applicant: Symrise AG, Holzminden (DE)

(72) Inventor: Gabriele Vielhaber, Colombes (FR)

(73) Assignee: Symrise AG, Holzminden (DE)

( * ) Notice: Subject to any disclaimer, the term of this patent is extended or adjusted under 35 U.S.C. 154(b) by 202 days.

(21) Appl. No.: 16/062,365

(22) PCT Filed: Dec. 15, 2015

(86) PCT No.: PCT/EP2015/079711
§ 371 (c)(1),
(2) Date: Jun. 14, 2018

(87) PCT Pub. No.: WO2017/101976
PCT Pub. Date: Jun. 22, 2017

(65) Prior Publication Data
US 2018/0369116 A1 Dec. 27, 2018

(51) Int. Cl.
| | |
|---|---|
| *A61K 8/64* | (2006.01) |
| *A61Q 17/04* | (2006.01) |
| *A61K 8/06* | (2006.01) |
| *A61K 8/27* | (2006.01) |
| *A61K 8/29* | (2006.01) |
| *A61K 8/35* | (2006.01) |
| *A61K 8/37* | (2006.01) |
| *A61K 8/41* | (2006.01) |
| *A61K 8/46* | (2006.01) |
| *A61Q 19/08* | (2006.01) |

(52) U.S. Cl.
CPC ............... *A61K 8/64* (2013.01); *A61K 8/06* (2013.01); *A61K 8/068* (2013.01); *A61K 8/27* (2013.01); *A61K 8/29* (2013.01); *A61K 8/35* (2013.01); *A61K 8/37* (2013.01); *A61K 8/41* (2013.01); *A61K 8/466* (2013.01); *A61Q 17/04* (2013.01); *A61Q 19/08* (2013.01); *A61K 2800/21* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 2006/0216251 A1 | 9/2006 | Morariu | |
| 2006/0286046 A1* | 12/2006 | Haber | A61K 8/447 424/59 |
| 2009/0017080 A1* | 1/2009 | Tanner | A61K 8/19 424/401 |
| 2014/0308222 A1 | 10/2014 | Dahlgren et al. | |

FOREIGN PATENT DOCUMENTS

| | | |
|---|---|---|
| EP | 1 388 339 A1 | 2/2004 |
| KR | 2002-0044740 A | 6/2002 |
| KR | 2004-0074795 A | 8/2004 |
| WO | 90/06102 A1 | 6/1990 |
| WO | 2014/128228 A2 | 8/2014 |

OTHER PUBLICATIONS

Larroque et al., "Elastin Modification by 4-Hydroxynonenal in Hairless Mice Exposed to UV-A. Role in Photoaging and Actinic Elastosis", Journal of Investigative Dermatology, vol. 135, pp. 1873-1881, Apr. 2015.*

* cited by examiner

*Primary Examiner* — Hasan S Ahmed
*Assistant Examiner* — Randeep Singh
(74) *Attorney, Agent, or Firm* — Dilworth & Barrese, LLP

(57) ABSTRACT

The invention relates to a preparation containing at least one compound of formula (I), providing that R1 is H or $CH_3$ and R2 is H or COOH, or salts thereof, to be used as a drug for preventing and/or treating signs of degeneration and ageing of the skin which are not, or not exclusively, caused by the effect of light.

12 Claims, No Drawings

PREPARATIONS COMPRISING CARNOSINES

FIELD OF THE INVENTION

The invention lies in the field of cosmetics or pharmaceutics and relates to the use of preparations having a content of carnosine and carnosine derivatives.

PRIOR ART

In the field of cosmetic products, the "anti-ageing" segment is certainly the most important at present, since the trend to appear as young as possible for as long as possible is continuing unabated among female consumers in particular. In order to satisfy this requirement, which is extremely interesting also economically, the cosmetics industry puts forward ever new active ingredients and active ingredient mixtures, some of which promise spectacular results in very short periods of time, without routinely making this tangible for the consumer.

Serious research knows, however, that the causes of sagging, rough, damaged and often simply aged skin are many and varied and—at least hitherto—cannot be at least alleviated by the use of a single active ingredient. Not even active ingredient cocktails, which address the various causes individually, are helpful here; the substances frequently hinder one another in their mechanisms of action.

There is therefore a continued need to find the cosmetic "philosopher's stone" which is able to counteract in one all the complaints mentioned above—from damage by UV rays to atony of the connective tissue. There is considerable doubt among experts as to whether this will be the case in the near future, even though understanding of the processes which take place in the skin is growing daily. Against this background, it would be very gratifying merely to be able to find a single substance which addresses at least some skin ageing phenomena, even if the markedness of the effects is not consistently at the same high level.

As has been mentioned, countless substances are known from the prior art to which an action in respect of skin damage is attributed. The substances which have hitherto been given less consideration for this purpose include carnosine and its compounds, which are actually typical food supplements. In reference to cosmetic applications in general and skin damage in particular, carnosine has hitherto only been associated with protection against UV rays.

It is known from a study by Aruoma et al. from 1989, for example, that carnosine is capable of capturing ROS (reactive oxygen species) [Biochem. J. 264(3), p. 863-869 (1989)]. According to a report by Babizhayev et al., carnosine is additionally able to capture alpha-beta-unsaturated aldehydes, which are liberated in the peroxidation of fatty acids of the cell membrane under oxidative stress [Membran & Cell Biol. 12(1), p. 89-99 (1998)].

Ultimately, however, the properties of carnosine in the field of skin care agents are based on its property as an antioxidant. Reference may also be made in this connection especially to publication WO 2014 128228 A2 (SYMRISE), which reveals the suitability of these substances for protecting against IR radiation on the basis of the inhibition of MMP expression.

In addition, there are known from EP 1591105 A1 (STADA) cosmetic and pharmaceutical preparations comprising an antioxidant, which preparations protect the skin against IR radiation. Among the many possible antioxidants, carnosine and arnesine are also mentioned. The compositions, which are to be administered topically, further comprise one or more inorganic and/or organic UV filters.

EP 2545898 A1 (COTY) discloses preparations which protect the skin against damage by IR radiation and thereby comprise plant extracts, vitamins, ruby powder, mica and titanium dioxide. In paragraph [0026], carnosine is also mentioned as a further suitable auxiliary substance, but as a radical acceptor.

EP 2181697 A2 (SHISEIDO) provides sunscreen agents in O/W form which are distinguished by a special cocktail of emulsifiers and sun protection filters. Table 3-3 discloses two compositions (Examples 22 and 23) which contain the combination of carnosine with UV filters.

WO 2010 124817 A2 (KPSS) relates to conditioning compositions for hair based, inter alia, on dipeptides such as, for example, carnosine. In the implementation examples there is a disclosure of the combination of carnosine with a UV filter, namely benzophenone-3.

EP 1310238 A2 (BASF) discloses cosmetic or dermatological sun protection agent preparations which comprise at least one cholesteric liquid-crystalline component which reflects in the infrared wavelength range of from 750 nm to 2500 nm, at least one filter substance which protects against radiation in the ultraviolet ray range of from 280 nm to 449 nm, and at least one cosmetically acceptable carrier, and the use thereof. Further antioxidants, such as, for example, carnosine, can additionally be present.

The object of the present was therefore to find a substance or a class of substances which is suitable in particular for preventing and treating signs of degeneration, in particular signs of ageing, of the skin which are not, or at least not exclusively, caused by the action of UV or IR radiation. Substances which stimulate the cellular repair functions and counteract damage to the skin caused by air pollution and ageing are of particular interest.

DESCRIPTION OF THE INVENTION

As first subject-matter, the invention provides a preparation comprising at least one compound of formula (I)

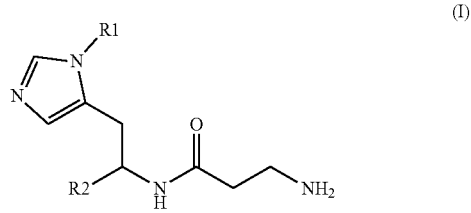

with the proviso that R1 represents H or $CH_3$ and R2 represents H or COOH, or salts thereof, for use as a medicament for preventing and/or treating signs of degeneration and of ageing of the skin which are not, or not exclusively, caused by the action of light.

As further subject-matter, the invention provides a preparation comprising (a) at least one compound of formula (I)

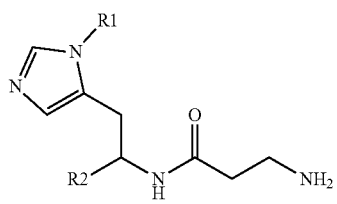

with the proviso that R1 represents H or $CH_3$ and R2 represents H or COOH, or salts thereof, and
(b) at least one UV sun protection factor for use as a medicament for preventing and/or treating signs of degeneration and of ageing of the skin which are not, or not exclusively, caused by the action of light.

Surprisingly, it has been found that carnosines, which hitherto were known only to have an anti-oxidative action in respect of the capture of oxygen radicals, are capable of positively influencing also other processes which take place at the skin surface or in the subcutaneous layer. These include in particular stimulating the formation of the enzyme G6PDH and thus, as a consequence, also increasing the production of intracellular DNA, both of which are important parameters for cell protection and skin renewal. It was particularly surprising that the activity could be increased further by the addition of UV sun protection filters, even though these substances on their own exhibit no activity.

It has further been found that, by the use of carnosines, apoptosis in human cell cultures and the content of free DNA fragments in the cytoplasm, and thus the degree of damaged DNA in the cell nucleus, decrease. Further in vitro findings indicate that carnosines have a regenerating and revitalizing activity in human fibroblasts and inhibit both the release of skin-damaging elastase and the glycation of collagen.

Active Ingredients

The active ingredients which are represented by formula (I) are compounds which are known in principle and which are accessible by conventional processes of organic chemistry. Preference is thereby given to the group of substances formed by carnosine, L-carnosine, D-carnosine, D/L-carnosine, carnicine, carnicine*HCl, anserine, D-anserine, L-anserine and L-anserine*$HNO_3$ and mixtures thereof.

According to the invention, salts of the compounds of formula (I) are preferably understood as being salts of the compounds of formula (I) with mineral acids, particularly preferably salts of formula (II):

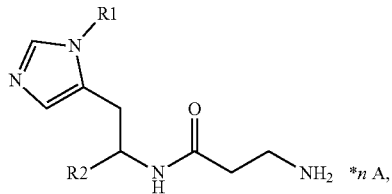

wherein n represents 1, 2 or 3 and A represents HCl or $HNO_3$ and R1 represents H or $CH_3$ and R2 represents H or COOH.

As mentioned above, the revitalizing and reactivating activity of the carnosines increases in particular the activity of G6PDH production and counteracts apoptosis. The use of the substances as protective and constructive medicaments or care products is possible in principle for all preparations which are used for prevention against damage or in the case of damage to the skin and thus in skin care and prophylaxis. Another use in this field is application to sensitive skin damaged by allergy or other causes. The damage to the skin can thereby have very different causes.

UV Sun Protection Factors

Mixtures of compounds of formula (I) or salts thereof with UV sun protection factors leads to a synergistic enhancement of the revitalization of the skin. The UV sun protection factors can be UV-A filters, UV-B filters, pigments or mixtures thereof, which are described in greater detail hereinbelow.

UV-A and UV-B Sun Protection Factors

UV sun protection factors are to be understood as being, for example, organic substances (sun protection filters) which are in liquid or crystalline form at room temperature and which are capable of absorbing ultraviolet rays and giving off the absorbed energy again in the form of long-wave radiation, for example heat. The UV sun protection factors are conventionally present in amounts of from 0.1 to 5% by weight and preferably from 0.2 to 1% by weight. UVB filters can be oil-soluble or water-soluble. There may be mentioned as oil-soluble substances, for example:

3-benzylidene camphor or 3-benzylidene norcamphor and derivatives thereof, for example 3-(4-methylbenzylidene) camphor described;

4-aminobenzoic acid derivatives, preferably 4-(dimethylamino)benzoic acid 2-ethylhexyl ester, 4-(dimethylamino)benzoic acid 2-octyl ester and 4-(dimethylamino)benzoic acid amyl ester;

esters of cinnamic acid, preferably 4-methoxycinnamic acid 2-ethylhexyl ester, 4-methoxycinnamic acid propyl ester, 4-methoxycinnamic acid isoamyl ester, 2-cyano-3,3-phenylcinnamic acid 2-ethylhexyl ester (octocrylene);

esters of salicylic acid, preferably salicylic acid 2-ethylhexyl ester, salicylic acid 4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzmalonic acid di-2-ethylhexyl ester;

triazine derivatives, such as, for example, 2,4,6-trianilino-(p-carbo-2'-ethyl-1'-hexyloxy)-1,3,5-triazine and octyl triazone or dioctyl butamido triazone (Uvasorb® HEB);

propane-1,3-diones, such as, for example 1-(4-tert-.butylphenyl)-3-(4'-methoxyphenyl)-propane-1,3-di-one;

ketotricyclo(5.2.1.0)decane derivatives.

There are suitable as water-soluble substances:

2-phenylbenzimidazole-5-sulfonic acid and the alkali, alkaline earth, ammonium, alkylammonium, alkanolammonium and glucammonium salts thereof;

1H-benzimidazole-4,6-disulfonic acid, 2,2'-(1,4-phenylene)bis-, disodium salt (Neo Heliopan® AP);

sulfonic acid derivatives of benzophenones, preferably 2-hydroxy-4-methoxybenzophenone-5-sulfonic acid and its salts;

sulfonic acid derivatives of 3-benzylidene camphor, such as, for example, 4-(2-oxo-3-bornylidenemethyl)benzene sulfonic acid and 2-methyl-5-(2-oxo-3-bornylidene)sulfonic acid and salts thereof.

As typical UV-A filters there are suitable in particular derivatives of benzoyl methane, such as, for example, 1-(4'-tert.butylphenyl)-3-(4'-methoxyphenyl)propane-1,3-dione, 4-tert.-butyl-4'-methoxy-dibenzoylmethane (Parsol® 1789), 2-(4-diethylamino-2-hydroxybenzoyl)-benzoic acid hexyl ester (Uvinul® A Plus), 1-phenyl-3-(4'-isopropylphenyl)-propane-1,3-dione, as well as enamine compounds. The UV-A and UV-B filters can of course also be used in mixtures. Particularly advantageous combinations consist of the derivatives of benzoylmethane, for example 4-tert.-butyl-4'-methoxydibenzoylmethane (Parsol® 1789) and 2-cyano-3,3-phenylcinnamic acid 2-ethylhexyl ester (octocrylene) in combination with esters of cinnamic acid, preferably 4-methoxycinnamic acid 2-ethylhexyl ester and/or 4-methoxycinnamic acid propyl ester and/or 4-methoxycinnamic acid isoamyl ester. Such combinations are advantageously combined with water-soluble filters such as, for example, 2-phenylbenzimidazole-5-sulfonic acid and the alkali, alkaline earth, ammonium, alkylammonium, alkanolammonium and glucammonium salts thereof.

Sun Protection Pigments

In addition to the mentioned soluble substances there are suitable for this purpose also insoluble sun protection pigments, namely finely disperse metal oxides or salts. Examples of suitable metal oxides are in particular zinc oxide and titanium dioxide and, in addition, oxides of iron, zirconium, silicon, manganese, aluminum and cerium and mixtures thereof. As salts there can be used silicates (talc), barium sulfate or zinc stearate. The oxides and salts are used in the form of the pigments for skin-care and skin-protecting emulsions and decorative cosmetics. The particles should thereby have a mean diameter of less than 100 nm, preferably between 5 and 50 nm and in particular between 15 and 30 nm. They can have a spherical shape, but it is also possible to use particles that have an ellipsoid shape or a shape which otherwise differs from the spherical form. The pigments can also be present in surface-treated, that is to say hydrophilized or hydrophobized, form. Typical examples are coated titanium dioxides, such as, for example titanium dioxide T 805 (Degussa) or Eusolex® T2000, Eusolex® T, Eusolex® T-ECO, Eusolex® T-S, Eusolex® T-Aqua, Eusolex® T-45D (all from Merck), Uvinul $TiO_2$ (BASF). There are suitable as hydrophobic coating agents especially silicones and in particular trialkoxyoctylsilanes or simethicone. In sunscreens, so-called micro- or nano-pigments are preferably used. Preference is given to the use of micronized zinc oxide such as, for example, Z-COTE® or Z-COTE HP1®.

Carriers

Both the medicaments and the cosmetic preparations described below can comprise as component (c) carriers, or solvents, selected from the group formed by water, alcohols, esters, butylene glycol, dipropylene glycol, ethanol, ethoxydiglycol, ethyl acetate, glycerol, propanol, isopropanol, macrogols, propylpropylene glycol(2) methyl ether, propylpropylene glycol(3) methyl ether, propylene carbonate, propylene glycol, triethylene glycol, isoparaffin, amyl acetate, amyl benzoate, benzyl acetate, butyl acetate, butylene glycol, butyl lactate, butooctyl benzoate, butooctyl salicylate, C10-C13 alkanes, C14-C17 alkanes, C11-C15 cycloalkanes, caprylyl butyrate, isoparaffins, diacetin, triacetin, dicaprylyl ether, dicaprylyl maleate and mixtures thereof.

Medicaments

The medicaments according to the invention comprise components (a) and (b) preferably in a weight ratio of from approximately 1:99 to approximately 99:1, in particular from approximately 5:95 to approximately 20:80 and most particularly preferably from approximately 10:90 to approximately 15:85. The synergy is most pronounced when the two components are used in a weight ratio of approximately 1:5.

A preferred medicament has the following composition:
(a) from approximately 0.001 to approximately 5% by weight, preferably from approximately 0.01 to approximately 1% by weight, further preferably approximately from 0.05 to 0.5% by weight and in particular from 0.1 to 0.25% by weight of a compound of formula (I), preferably carnosine,
(b) 0 or from approximately 0.05 to approximately 20% by weight, preferably from approximately 0.1 to approximately 10% by weight and in particular from approximately 1 to approximately 5% by weight of at least one UV sun protection factor, and
(c) ad 100% by weight carriers.

Cosmetic Preparations

The present invention further provides cosmetic agents for treating signs of degeneration and in particular of ageing of the skin which are not, or not exclusively, based on the influence of light, which agents comprise
(a) at least one compound of formula (I)

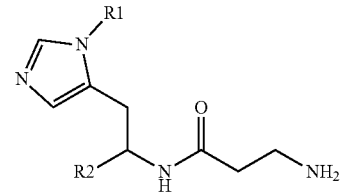

with the proviso that R1 represents H or $CH_3$ and R2 represents H or COOH, or salts thereof, and
(b) at least one UV sun protection factor, preferably at least one UV-A and at least one UV-B sun protection factor, and optionally
(c1) carriers,
(c2) oily substances, and/or
(c3) emulsifiers.

The preparations according to the invention are preferably in the form of creams, lotions, gels, pastes or capsules and are in particular anti-ageing agents.

It is further preferred that component (a) is present in amounts of from 0.001 to approximately 5% by weight, preferably from approximately 0.01 to approximately 1% by weight, further preferably approximately from 0.05 to 0.5% by weight and in particular from 0.1 to 0.25% by weight, based on the total composition. The amount of component (b) can exceed that of component (a) by a factor of from approximately 2 to approximately 20, in particular from approximately 5 to approximately 15 and in particular from approximately 8 to approximately 10.

The agents according to the invention can comprise further typical auxiliary substances and additives, such as, for example, mild surfactants, oily substances, emulsifiers, pearlescent waxes, consistency regulators, thickeners, superfatting agents, stabilizers, polymers, silicone compounds, fats, waxes, lecithins, phospholipids, humectants, biogenic active ingredients, antioxidants, deodorants, antiperspirants, self-tanning agents, tyrosine inhibitors (depigmenting agents), hydrotropes, solubilizers, preservatives, perfume oils, dyes and the like.

Surfactants

Anionic, non-ionic, cationic and/or amphoteric or zwitterionic surfactants can be present as surface-active substances, the amount of which in the agents is conventionally approximately from 1 to 70% by weight, preferably from 5 to 50% by weight and in particular from 10 to 30% by weight. Typical examples of anionic surfactants are soaps, alkyl benzenesulfonates, alkane sulfonates, olefin sulfonates, alkyl ether sulfonates, glycerol ether sulfonates, α-methyl ester sulfonates, sulfo fatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and di-alkyl sulfosuccinates, mono- and di-alkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyloligoglucoside sulfates, protein fatty acid condensates (in particular wheat-based plant products), and alkyl (ether) phosphates. If the anionic surfactants contain polyglycol ether chains, they can have a conventional, but preferably narrow, homolog distribution. Typical examples of non-ionic surfactants are fatty alcohol polyglycol ethers, alkyl phenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolyzates (in particular wheat-based plant products), polyol fatty acid esters, sugar esters, sorbitan esters, polysorbates and amine oxides. If the non-ionic surfactants contain polyglycol ether chains, they can have a conventional, but preferably narrow, homolog distribution. Typical examples of cationic surfactants are quaternary ammonium compounds, such as, for example, dimethyldistearylammonium chloride, and esterquats, in particular quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The mentioned surfactants are all known compounds. Typical examples of particularly suitable mild surfactants, that is to say surfactants that are particularly well tolerated by the skin, are fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, the latter preferably based on wheat proteins.

Oily Substances

There come into consideration as oily substances, for example, Guerbet alcohols based on fatty alcohols having from 6 to 18, preferably from 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethyl hexanol, esters of $C_{18}$-$C_{38}$-alkylhydroxycarboxylic acids with linear or branched $C_6$-$C_{22}$-fatty alcohols, in particular dioctyl malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/tri-glyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having from 1 to 22 carbon atoms or polyols having from 2 to 10 carbon atoms and from 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having from 6 to 18, preferably from 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having from 6 to 22 carbon atoms per alkyl group, such as, for example, dicaprylyl ether (Cetiol® OE), ring-opening products of epoxidized fatty acids with polyols, silicone oils (cyclomethicone, silicon methicone types inter alia) and/or aliphatic or naphthenic hydrocarbons, such as, for example, squalane, squalene or dialkylcyclohexanes.

Emulsifiers

There are suitable as emulsifiers, for example, non-ionic surfactants from at least one of the following groups:
  addition products of from 2 to 30 mol of ethylene oxide and/or from 0 to 5 mol of propylene oxide with linear fatty alcohols having from 8 to 22 carbon atoms, with fatty acids having from 12 to 22 carbon atoms, with alkylphenols having from 8 to 15 carbon atoms in the alkyl group, as well as alkylamines having from 8 to 22 carbon atoms in the alkyl moiety;
  alkyl and/or alkenyl oligoglycosides having from 8 to 22 carbon atoms in the alk(en)yl moiety, and ethoxylated analogs thereof;
  addition products of from 1 to 15 mol of ethylene oxide with castor oil and/or hardened castor oil;
  addition products of from 15 to 60 mol of ethylene oxide with castor oil and/or hardened castor oil;
  partial esters of glycerol and/or sorbitan with unsaturated, linear or saturated, branched fatty acids having from 12 to 22 carbon atoms and/or hydroxycarboxylic acids having from 3 to 18 carbon atoms, as well as adducts thereof with from 1 to 30 mol of ethylene oxide;
  partial esters of polyglycerol (average inherent degree of condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside) as well as polyglucosides (e.g. cellulose) with saturated and/or unsaturated, linear or branched fatty acids having from 12 to 22 carbon atoms and/or hydroxycarboxylic acids having from 3 to 18 carbon atoms, as well as adducts thereof with from 1 to 30 mol of ethylene oxide;

mixed esters of pentaerythritol, fatty acids, citric acid and fatty alcohol and/or mixed esters of fatty acids having from 6 to 22 carbon atoms, methylglucose and polyols, preferably glycerol or polyglycerol;

mono-, di- and tri-alkyl phosphates as well as mono-, di- and/or tri-PEG-alkyl phosphates and salts thereof;

wool wax alcohols;

polysiloxane-polyalkyl-polyether copolymers or corresponding derivatives;

block copolymers, for example polyethylene glycol-30 dipolyhydroxystearate;

polymeric emulsifiers, for example Pemulen types (TR-1, TR-2) from Goodrich or Cosmedia® SP from Cognis;

polyalkylene glycols; and glycerol carbonate.

Particularly suitable emulsifiers are discussed in greater detail hereinbelow:

Alkoxylates.

The addition products of ethylene oxide and/or propylene oxide with fatty alcohols, fatty acids, alkylphenols or with castor oil are known products which are available commercially. They are homolog mixtures whose mean degree of alkoxylation corresponds to the ratio of the amounts of ethylene oxide and/or propylene oxide and substrate with which the addition reaction is carried out. $C_{12/18}$-Fatty acid mono- and di-esters of addition products of ethylene oxide with glycerol are known as refatting agents for cosmetic preparations.

Alkyl and/or Alkenyl Oligoglycoside.

Alkyl and/or alkenyl oligoglycosides, their preparation and their use are known from the prior art. They are prepared in particular by reaction of glucose or oligosaccharides with primary alcohols having from 8 to 18 carbon atoms. With regard to the glycoside radical, both monoglycosides, in which a cyclic sugar residue is glycosidically bonded to the fatty alcohol, and oligomeric glycosides having a degree of oligomerization up to preferably approximately 8 are suitable. The degree of oligomerization is a statistical mean based on a conventional homolog distribution for such commercial products.

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride and commercial mixtures thereof which, subordinately from the preparation process, may still contain small amounts of triglyceride. Also suitable are addition products of from 1 to 30 mol, preferably from 5 to 10 mol, of ethylene oxide with the mentioned partial glycerides.

Sorbitan Esters.

There come as sorbitan esters sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and commercial mixtures thereof. Also suitable are addition products of from 1 to 30 mol, preferably from 5 to 10 mol, of ethylene oxide with the mentioned sorbitan esters.

Polyglycerol Esters.

Typical examples of suitable polyglycerol esters are polyglyceryl-2 dipolyhydroxy stearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate and mixtures thereof. Examples of further suitable polyol esters are the mono-, di- and tri-esters, optionally reacted with from 1 to 30 mol of ethylene oxide, of trimethylol propane or pentaerythritol with lauric acid, coconut fatty acid, tallow fatty acid, palmitic acid, stearic acid, oleic acid, behenic acid and the like.

Anionic Emulsifiers.

Typical anionic emulsifiers are aliphatic fatty acids having from 12 to 22 carbon atoms, such as, for example, palmitic acid, stearic acid or behenic acid, as well as dicarboxylic acids having from 12 to 22 carbon atoms, such as, for example, azelaic acid or sebacic acid.

Amphoteric and Cationic Emulsifiers.

Zwitterionic surfactants can further be used as emulsifiers. Zwitterionic surfactants denotes those surface-active compounds that carry at least one quaternary ammonium group and at least one carboxylate group and one sulfonate group in the molecule. Particularly suitable zwitterionic surfactants are the so-called betaines such as the N-alkyl N,N-dimethylammoniumglycinates, for example coco alkyldimethylammoniumglycinate, N-acylaminopropyl N,N-dimethylammoniumglycinate, for example coco acylaminopropyl dimethylammoniumglycinate, and 2-alkyl-3-carboxylmethyl-3-hydroxyethylimidazolines each having from 8 to 18 carbon atoms in the alkyl or acyl group, as well as coco acylaminoethyl hydroxyethyl carboxymethyl glycinate. Particular preference is given to the fatty acid amide derivative known by the CTFA name Cocamidopropyl Betaine. Ampholytic surfactants are likewise suitable emulsifiers. Ampholytic surfactants are understood as being those surface-active compounds that contain in the molecule, in addition to a $C_{8/18}$-alkyl or -acyl group, at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkylimino-dipropionic acids, N-hydroxyethyl-N-alkylamidopropylglycine, N-alkyltaurines, N-alkylsarcosines, 2-alkylaminopropionic acids and alkylaminoacetic acids each having approximately from 8 to 18 carbon atoms in the alkyl group. Particularly preferred ampholytic surfactants are N-coco alkylaminopropionate, coco acylaminoethylamino propionate and $C_{12/18}$-acylsarcosine. Finally, cationic surfactants also come into consideration as emulsifiers, whereby those of the esterquat type, especially methylquaternized di-fatty acid triethanolamine ester salts, are particularly preferred.

Fats and Waxes

Typical examples of fats are glycerides, that is to say solid or liquid vegetable or animal products which consist substantially of mixed glycerol esters of higher fatty acids, as waxes there are suitable inter alia natural waxes, such as, for example, candelilla wax, carnauba wax, Japan wax, esparto wax, cork wax, guaruma wax, rice germ oil wax, sugarcane wax, ouricury wax, montan wax, beeswax, shellac wax, sperm whale oil, lanolin (wool wax), preen oil, ceresin, ozokerite (earth wax), petrolatum, paraffin waxes, microwaxes; chemically modified waxes (hard waxes), such as, for example, montan ester waxes, Sasol waxes, hydrogenated jojoba waxes as well as synthetic waxes, such as, for example, polyalkylene waxes and polyethylene glycol waxes. In addition to the fats, fat-like substances, such as lecithins and phospholipids, are also suitable as additives. The person skilled in the art will understand the term lecithins as meaning those glycero-phospholipids which are formed from fatty acids, glycerol, phosphoric acid and choline by esterification. Lecithins are therefore frequently also among experts as phosphatidylcholines (PC). There may be mentioned as examples of natural lecithins the cephalins, which are also referred to as phosphatidic acids and are derivatives of 1,2-diacyl-sn-glycerol-3-phosphoric acids. By contrast, phospholipids are usually understood as being mono- and preferably di-esters of phosphoric acid with glycerol (glycerol phosphates), which are generally included among the fats. In addition, sphingosines or sphingolipids are also suitable.

Pearlescent Waxes

There are suitable as pearlescent waxes, for example: alkylene glycol esters, especially ethylene glycol distearate; fatty acid alkanolamides, especially coconut fatty acid diethanolamide; partial glycerides, especially stearic acid monoglyceride; esters of polyvalent, optionally hydroxy-substituted carboxylic acids with fatty alcohols having from 6 to 22 carbon atoms, especially long-chain esters of tartaric acid; fatty substances, such as, for example, fatty alcohols, fatty ketones, fatty aldehydes, fatty ethers and fatty carbonates, which contain at least 24 carbon atoms in total, especially laurone and distearyl ether; fatty acids such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxyl groups, and mixtures thereof.

Cooling Substances

Cooling substances are compounds which produce a sensation of coolness on the skin. Generally, such substances are menthol compounds which—in addition to the menthol basic structure itself—for example selected from the group formed by menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomethyl glutamate (FEMA GRAS 4006), menthoxy-1,2-propanediol (FEMA GRAS 3784), menthoxy-2-methyl-1,2-propanediol (FEMA GRAS 3849) and also the menthanecarboxylic acid esters and amides WS-3, WS-4, WS-5, WS-12, WS-14 and WS-30 and mixtures thereof.

[1] FEMA stands for "Flavor and Extracts Manufacturers Association" and GRAS is defined as "Generally Regarded As Safe". A FEMA GRAS designation means that the substance so characterized is tested according to a standard method and is considered toxicologically harmless.

A first important representative of these substances is monomethyl succinate (FEMA GRAS 3810). Both the succinate and the analogous monomethyl glutarate (FEMA GRAS 4006) are important representatives of monomethyl esters based on di- and poly-carboxylic acids:

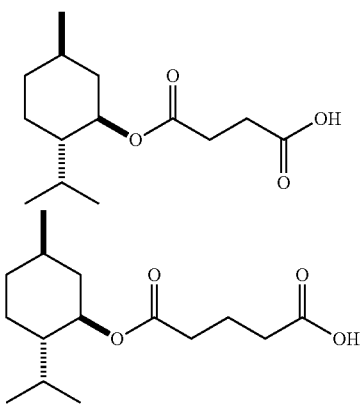

Examples of applications of these substances are to be found, for example, in publications WO 2003 043431 (Unilever) or EP 1332772 A1 (IFF).

The next important group of menthol compounds which are preferred within the meaning of the invention comprises carbonate esters of menthol and polyols, such as, for example, glycols, glycerol or carbohydrates, such as, for example, menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives. Likewise preferred are the menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is marketed under the name Frescolat® MGA. Among these substances, menthone glyceryl acetal/ketal and menthyl lactate as well as menthol ethylene glycol carbonate or menthol propylene glycol carbonate, which are marketed by the applicant under the names Frescolat® MGA, Frescolat® ML, Frescolat® MGC and Frescolat® MPC, have been found to be most particularly advantageous.

In the 70s of the last century, menthol compounds having a C—C bond in the 3-position were developed for the first time, and a number of representatives of these compounds can likewise be used. These substances are referred to generally as WS types. The basic structure is a menthol derivative in which the hydroxyl group has been replaced by a carboxyl group (WS-1). All further WS types, such as, for example, the preferred species WS-3, WS-4, WS-5, WS-12, WS-14 and WS-30, are derived from that structure.

Consistency Regulators and Thickeners

There come into consideration as consistency regulators primarily fatty alcohols or hydroxy fatty alcohols having from 12 to 22 and preferably from 16 to 18 carbon atoms and, in addition, partial glycerides, fatty acids or hydroxy fatty acids. Preference is given to a combination of these substances with alkyl oligoglucosides and/or fatty acid N-methylglucamides of equal chain length and/or polyglycerol poly-12-hydroxystearates. Suitable thickeners are, for example, Aerosil types (hydrophilic silicas), polysaccharides, in particular xanthan gum, guar-guar, agar-agar, alginates and tyloses, carboxymethylcellulose and hydroxyethyl- and hydroxypropyl-cellulose, also higher molecular weight polyethylene glycol mono- and di-esters of fatty acids, polyacrylates (e.g. Carbopols® and Pemulen types from Goodrich; Synthalens® from Sigma; Keltrol types from Kelco; Sepigel types from Seppic; Salcare types from Allied Colloids), polyacrylamides, polymers, polyvinyl alcohol and polyvinylpyrrolidone. Bentonites, such as, for example, Bentone® Gel VS-5PC (Rheox), which is a mixture of cyclopentasiloxane, disteardimonium hectorite and propylene carbonate, have also been found to be particularly effective. There are also suitable surfactants, such as, for example, ethoxylated fatty acid glycerides, esters of fatty acids with polyols such as, for example, pentaerythritol or trimethylolpropane, fatty alcohol ethoxylates with narrow homolog distribution or alkyl oligoglucosides, as well as electrolytes such as sodium chloride and ammonium chloride.

Superfatting Agents and Stabilizers

As superfatting agents there can be used substances such as, for example, lanolin and lecithin as well as polyethoxylated or acylated lanolin and lecithin derivatives, polyol fatty acid esters, monoglycerides and fatty acid alkanolamides, whereby the latter at the same time serve as foam stabilizers.

As stabilizers there can be used metal salts of fatty acids, such as, for example, magnesium, aluminum and/or zinc stearate or ricinoleate.

Polymers

Suitable cationic polymers are, for example, cationic cellulose derivatives, such as, for example, a quaternized hydroxyethylcellulose which is obtainable under the name Polymer JR 400® from Amerchol, cationic starches, copolymers of diallylammonium salts and acrylamides, quaternized vinylpyrrolidone/vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat® L/Grünau), quaternized wheat polypeptides, polyethyleneimine, cationic silicone polymers, such as, for example, amodimethicone, copolymers of adipic acid and dimethylaminohydroxypropyldiethylenetriamine (Cartaretine®/Sandoz), copolymers of acrylic acid with dimethyl-diallylammonium chloride (Merquat® 550/Chemviron), polyaminopolyamides and crosslinked water-soluble polymers thereof, cationic chitin derivatives such as, for example, quaternized chitosan, optionally distributed in microcrystalline form, condensation products of dihaloalkyls, such as, for example, dibromobutane, with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

There are suitable as anionic, zwitterionic, amphoteric and non-ionic polymers, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked and polyol-crosslinked polyacrylic acids, acrylamidopropyltrimethylammonium chloride/acrylate copolymers, octylacryl-amide/methyl methacrylate/tert.butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers as well as optionally derivatized cellulose ethers and silicones.

Silicone Compounds

Suitable silicone compounds are, for example, dimethylpolysiloxanes, methylphenylpolysiloxanes, cyclic silicones as well as amino-, fatty acid-, alcohol-, polyether-, epoxy-, fluorine-, glycoside- and/or alkyl-modified silicone compounds, which can be in both liquid and resin-like form at room temperature. Also suitable are simethicones, which are mixtures of dimethicones having an average chain length of from 200 to 300 dimethylsiloxane units and hydrogenated silicates.

Humectants

Humectants serve for further optimizing the sensory properties of the composition as well as for regulating the moisture content of the skin. At the same time, the low-temperature stability of the preparations according to the invention, in particular in the case of emulsions, is increased. The humectants are conventionally present in an amount of from 0.1 to 15% by weight, preferably from 1 to 10% by weight and in particular from 5 to 10% by weight.

There are suitable according to the invention inter alia amino acids, pyrrolidonecarboxylic acid, lactic acid and salts thereof, lactitol, urea and urea derivatives, uric acid, glucosamine, creatinine, cleavage products of collagen, chitosan or chitosan salts/derivatives, and in particular polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbitylsilanediol, sucrose, trehalose, xylose, xylitol, glucuronic acid and salts thereof), ethoxylated sorbitol (sorbeth-6, sorbeth-20, sorbeth-30, sorbeth-40), honey and hardened honey, hardened starch hydrolyzates as well as mixtures of hardened wheat protein and PEG-20-acetate copolymer. Glycerol, diglycerol, triglycerol and butylene glycol are preferably suitable according to the invention as humectants.

Biogenic Active Ingredients and Antioxidants

Biogenic active ingredients are to be understood as being, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, plum extract, Bambara nut extract and vitamin complexes.

Antioxidants interrupt the photochemical reaction chain which is initiated when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopine) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) as well as salts thereof, dilauryl thiodipropionate, distearyl thiodipropionate, thiodipropionic acid and derivatives thereof (esters, ethers, peptides, lipids, nucleotides, nucleosides and salts) as well as sulfoximine compounds (e.g. buthionine sulfoximine, homocysteine sulfoximine, butionine sulfone, penta-, hexa-, hepta-thionine sulfoximine) in very small tolerable doses (e.g. pmol to µmol/kg), also (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) as well as coniferyl benzoate of benzoin, rutic acid and derivatives thereof, α-glycosylrutin, ferulic acid, furfurylidene glucitol, carnosine, butylhydroxytoluene, butylhydroxyanisole, nordihydroguaiaresin acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO$_4$) selenium and derivatives thereof (e.g. selenium methionine), stilbene and derivatives thereof (e.g. stilbene oxide, trans-stilbene oxide) and the derivatives of those mentioned active ingredients that are suitable according to the invention (salts, esters, ethers, sugars, nucleotides, nucleosides, peptides and lipids).

Deodorants and Bacteriostatic Agents

Cosmetic deodorants counteract body odors, mask or eliminate them. Body odors arise due to the action of skin bacteria on apocrine sweat, whereby malodorous degradation products are formed. Deodorants accordingly comprise active ingredients which act as bacteriostatic agents, enzyme inhibitors, odor absorbers or odor-masking agents.

Bacteriostatic Agents.

There are suitable as bacteriostatic agents in principle any substances which are active against gram-positive bacteria, such as, for example, 4-hydroxybenzoic acid and its salts and esters, N-(4-chlorophenyl)-N'-(3,4-dichlorophenyl) urea, 2,4,4'-trichloro-2'-hydroxy-diphenyl ether (Triclosan), 4-chloro-3,5-dimethyl-phenol, 2,2'-methylene-bis(6-bromo-4-chlorophenol), 3-methyl-4-(1-methylethyl)-phenol, 2-benzyl-4-chlorophenol, 3-(4-chlorophenoxy)-1,2-propanediol, 3-iodo-2-propynylbutylcarbamate, chlorhexidine, 3,4,4'-trichlorocarbanilide (TTC), antibacterial fragrances, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid N-alkylamides such as, for example, salicylic acid n-octylamide or salicylic acid n-decylamide.

Enzyme Inhibitors.

Esterase inhibitors, for example, are suitable as enzyme inhibitors. They are preferably trialkyl citrates such as trimethyl citrate, tripropyl citrate, triisopropyl citrate, tributyl citrate and in particular triethyl citrate (Hydagen® CAT). The substances inhibit enzyme activity and thereby reduce odor formation. Further substances which come into consideration as esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof such as, for example, citric acid, malic acid, tartaric acid or tartaric acid diethyl ester, as well as zinc glycinate.

Odor Absorbers.

There are suitable as odor absorbers substances which are able to absorb and largely retain odor-forming compounds. They lower the partial pressure of the individual components and thus also reduce the rate at which they spread. It is important that perfumes thereby remain unimpaired. Odor absorbers are not effective against bacteria. They comprise as the main constituent, for example, a complex zinc salt of ricinoleic acid or special, largely odor-neutral fragrances, which are known to the person skilled in the art as "fixateurs", such as, for example, extracts of labdanum or styrax or specific abietic acid derivatives. Fragrances or perfume oils which, in addition to their function as odor-masking agents, impart to the deodorants their particular fragrance note act as odor-masking agents. There may be mentioned as perfume oils, for example, mixtures of natural and synthetic fragrances. Natural fragrances are extracts of blossoms, stems and leaves, fruits, fruit skins, roots, woods, herbs and grasses, needles and branches as well as resins and balsams. Animal raw materials are also suitable, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert.-butyl cyclohexyl acetate, linalyl acetate, phenylethyl acetate, linalyl benzoate, benzyl formate, allyl cyclohexyl propionate, styrallyl propionate and benzyl salicylate. The ethers include, for example, benzyl ethyl ether, the aldehydes include, for example, the linear alkanals having from 8 to 18 carbon atoms, citral, citronellal, citronellyl oxyacetaldehyde, cyclamen aldehyde, hydroxycitronellal, lilial and bourgeonal, the ketones include, for example, the ionones and methyl cedryl ketone, the alcohols include anethol, citronellol, eugenol, isoeugenol, geraniol, linalool, phenylethyl alcohol and terpineol, the hydrocarbons include mainly the terpenes and balsams. Preference is given, however, to the use of mixtures of different fragrances which together produce an appealing fragrance note. Essential oils of relatively low volatility, which are used mostly as flavor components, are also suitable as perfume oils, for example sage oil, camomile oil, clove oil, melissa oil, mint oil, cinnamon leaf oil, lime blossom oil, juniper berry oil, vetiver oil, olibanum oil, galbanum oil, labdanum oil and lavandin oil. Preference is given to the use of bergamot oil, dihydromyrcenol, lilial, lyral, citronellol, phenylethyl alcohol, α-hexyl cinnamaldehyde, geraniol, benzylacetone, cyclamen aldehyde, linalool, Boisambrene Forte, Ambroxan, indole, hedione, sandelice, lemon oil, mandarin oil, orange oil, allylamyl glycolate, cyclovertal, lavandin oil, clary sage oil, β-damascone, geranium oil bourbon, cyclohexyl salicylate, Vertofix Coeur, Iso-E-Super, Fixolide NP, evernyl, iraldeine gamma, phenylacetic acid, geranyl acetate, benzyl acetate, rose oxide, romilat, irotyl and floramat, on their own or in mixtures.

Antiperspirants.

Antiperspirants reduce perspiration by influencing the activity of the eccrine sweat glands and thus counteract underarm wetness and body odor. Aqueous or water-free formulations of antiperspirants typically comprise the following ingredients:

astringent active ingredients,
oil components,
non-ionic emulsifiers,
co-emulsifiers,
consistency regulators, auxiliary substances such as, for example, thickeners or complexing agents, and/or non-aqueous solvents such as, for example, ethanol, propylene glycol and/or glycerol.

There are suitable as astringent antiperspirant active ingredients primarily salts of aluminum, zirconium or zinc. Suitable active ingredients having antihidrotic activity of this type are, for example, aluminum chloride, aluminum chlorohydrate, aluminum dichlorohydrate, aluminum sesquichlorohydrate and complex compounds thereof, for example with 1,2-propylene glycol. Aluminum hydroxyallantoinate, aluminum chloride tartrate, aluminum-zirconium trichlorohydrate, aluminum-zirconium tetrachlorohydrate, aluminum-zirconium pentachlorohydrate and complex compounds thereof, for example with amino acids such as glycine. Oil-soluble and water-soluble auxiliary substances conventional in antiperspirants can additionally be present in lesser amounts. Such oil-soluble active ingredients can be, for example:

anti-inflammatory, skin-protecting or fragrant essential oils, synthetic skin-protecting active ingredients, and/or oil-soluble perfume oils.

Conventional water-soluble additives are, for example, preservatives, water-soluble fragrances, agents for adjusting the pH, for example buffer mixtures, water-soluble thickeners, for example water-soluble natural or synthetic polymers such as, for example, xanthan gum, hydroxyethylcellulose, polyvinylpyrrolidone or high molecular weight polyethylene oxides.

Hydrotropes

In order to improve the flow behavior, hydrotropes, such as, for example, ethanol, isopropyl alcohol, or polyols, can also be used; these substances largely correspond to the carriers described at the beginning. Polyols which come into consideration here preferably have from 2 to 15 carbon atoms and at least two hydroxyl groups. The polyols can contain further functional groups, in particular amino groups, or be modified with nitrogen. Typical examples are glycerol;

alkylene glycols, such as, for example, ethylene glycol, diethylene glycol, propylene glycol, butylene glycol, hexylene glycol as well as polyethylene glycols having an average molecular weight of from 100 to 1000 daltons;

commercial oligoglycerol mixtures having an inherent degree of condensation of from 1.5 to 10 such as, for example, commercial diglycerol mixtures having a diglycerol content of from 40 to 50% by weight;

methylol compounds, such as in particular trimethylolethane, trimethylolpropane, trimethylol butane, pentaerythritol and dipentaerythritol;

lower alkyl glucosides, in particular those having from 1 to 8 carbon atoms in the alkyl moiety, such as, for example, methyl and butyl glucoside;

sugar alcohols having from 5 to 12 carbon atoms, such as, for example, sorbitol or mannitol;

sugars having from 5 to 12 carbon atoms, such as, for example, glucose or sucrose;

amino sugars, such as, for example, glucamine;

dialcohol amines, such as diethanolamine or 2-amino-1,3-propanediol.

Preservatives

There are suitable as preservatives, for example, phenoxyethanol, formaldehyde solution, parabens, pentanediol or sorbic acid as well as the silver complexes known by the name Surfacine® and the further substance classes listed in Annex 6, Parts A and B of the Kosmetikverordnung (Cosmetics Directive).

Perfume Oils and Flavorings

There may be mentioned as perfume oils mixtures of natural and synthetic fragrances. Natural fragrances are extracts of blossoms (lily, lavender, rose, jasmine, neroli, ylang-ylang), stems and leaves (geranium, patchouli, petitgrain), fruits (anise, coriander, caraway, juniper), fruit skins (bergamot, lemon, orange), roots (nutmeg, angelica, celery, cardamon, costus, iris, calamus), woods (pinewood, sandalwood, guaiac wood, cedarwood, rosewood), herbs and grasses (tarragon, lemongrass, sage, thyme), needles and branches (spruce, fir, pine, mountain pine), resins and balsams (galbanum, elemi, benzoin, myrrh, olibanum, opoponax). Animal raw materials are also suitable, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert.butyl cyclohexyl acetate, linalyl acetate, dimethyl benzyl carbinyl acetate, phenylethyl acetate, linalyl benzoate, benzyl formate, ethylmethyl phenyl glycinate, allyl cyclohexyl propionate, styrallyl propionate and benzyl salicylate. The ethers include, for example, benzyl ethyl ether, the aldehydes include, for example, the linear alkanals having from 8 to 18 carbon atoms, citral, citronellal, citronellyl oxyacetaldehyde, cyclamen aldehyde, hydroxycitronellal, lilial and bourgeonal, the ketones include, for example, the ionones, α-isomethylionone and methyl cedryl ketone, the alcohols include anethol, citronellol, eugenol, isoeugenol, geraniol, linalool, phenylethyl alcohol and terpineol, the hydrocarbons include mainly the terpenes and balsams. Preference is given, however, to the use of mixtures of different fragrances which together produce an appealing fragrance note. Essential oils of relatively low volatility, which are used mostly as flavor components, are also suitable as perfume oils, for example sage oil, camomile oil, clove oil, melissa oil, mint oil, cinnamon leaf oil, lime blossom oil, juniper berry oil, vetiver oil, olibanum oil, galbanum oil, ladanum oil and lavandin oil. Preference is given to the use of bergamot oil, dihydromyrcenol, lilial, lyral, citronellol, phenylethyl alcohol, α-hexyl cinnamaldehyde, geraniol, benzylacetone, cyclamen aldehyde, linalool, Boisambrene Forte, Ambroxan, indole, hedione, sandelice, lemon oil, mandarin oil, orange oil, allylamyl glycolate, cyclovertal, lavandin oil, clary sage oil, β-damascone, geraniol oil bourbon, cyclohexyl salicylate, Vertofix Coeur, Iso-E-Super, Fixolide NP, evernyl, iraldeine gamma, phenylacetic acid, geranyl acetate, benzyl acetate, rose oxide, romillat, irotyl and floramat, on their own or in mixtures.

There are suitable as flavorings, for example, peppermint oil, spearmint oil, anise oil, star anise oil, caraway oil, eucalyptus oil, fennel oil, lemon oil, wintergreen oil, clove oil, menthol and the like.

Dyes

There can be used as dyes the substances that are suitable and authorized for cosmetic purposes, as are listed, for example, in the publication "Kosmetische Färbemittel" der Farbstoffkommission der Deutschen Forschungsgemeinschaft, Verlag Chemie, Weinheim, 1984, p. 81-106. Examples are Cochineal Red A (C.I. 16255), Patent Blue V (C.I. 42051), Indigotine (C.I. 73015), Chlorophylline (C.I. 75810), Quinoline Yellow (C.I. 47005), titanium dioxide (C.I. 77891), Indanthrene Blue RS (C.I. 69800) and Madder Lake (C.I. 58000). Luminol can also be present as a luminescent dye. These dyes are conventionally used in concentrations of from 0.001 to 0.1% by weight, based on the total mixture.

The total amount of auxiliary substances and additives can be from 1 to 50% by weight, preferably from 5 to 40% by weight, based on the compositions. The preparation of the compositions can be carried out by conventional cold or hot processes; the phase inversion temperature method is preferably followed.

INDUSTRIAL APPLICABILITY

As further subject-matter, the invention provides a non-therapeutic method of preventing and/or treating human skin against signs of degeneration and of ageing which are not, or not exclusively, caused by the influence of light, in which a preparation according to the first or second subject-matter of the invention or a cosmetic agent of the type described at the beginning is applied topically. It has been found that the topical administration of from approximately 1 to approximately 5 g of these preparations or agents at least once, better twice, daily for a period of at least from 7 to 14 days leads to measurable results, in particular as regards the depth of wrinkles. The preparations and agents are found to be particularly effective in female consumers of from 35 to 55 years of age.

Also claimed is the use of at least one compound of formula (I)

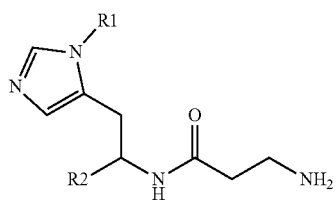

with the proviso that R1 represents H or $CH_3$ and R2 represents H or COOH, or salts thereof, for preventing and/or treating signs of degeneration and of ageing of human skin which are not, or not exclusively, caused by the influence of light. The use can optionally take place in combination with UV sun protection factors.

In particular, this use also comprises
  stimulating G6PDH activity and thus increasing the amount of cellular DNA,
  inhibiting apoptosis induction,
  stimulating the production of dermal macromolecules,
  inhibiting elastase activity, and
  inhibiting the glycation of collagen,
as is described in detail in the following examples.

Dermal Macromolecules

The present invention influences the formation of dermal macromolecules, the degradation of which in turn represents an important cause of skin ageing or skin degeneration. The relationships will be discussed briefly hereinbelow.

Within the meaning of the invention, dermal macromolecules are to be understood in principle as being all macromolecules which are to be found as constituents of the skin either in the basal membrane between the dermis and the epidermis or in the dermis and epidermis directly. The dermal macromolecules are in particular those which are selected from the group formed by glycosaminoglycans, in particular chondroitin sulfate, keratan sulfate, dermatan sulfate and hyaluronic acid and salts thereof, collagen, in particular type III collagen, elastin, fibronectin, proteoglycans and salts thereof.

The glycosaminoglycans are also referred to as mucopolysaccharides. They are negatively charged, long unbranched polysaccharides (glycans), which consist of 1,4-linked units of disaccharides in which one mole of a uronic acid (D-glucuronic acid or, for example, L-iduronic acid) is glycosidically bonded with the 3-position of an N-acetylated amino sugar (glycosamine). The glycosaminoglycans are attached in tissue as a plurality of chains to a core protein and thus form the proteoglycans.

Chondroitin sulfate is one of the glycosaminoglycans. It occurs in tissue as chondroitin 4-sulfate or as chondroitin 6-sulfate and consists inter alia of D-glucuronic acid and N-acetyl-D-galactosamine. Its molar mass is between 5000 and 50,000. The glycosaminoglycan dermatan sulfate, also known as beta-heparin, which has non-anticoagulant activity, consists of L-iduronic acid or D-glucuronic acid, N-acetyl-D-galactosamine and sulfate groups. The molar mass of dermatan sulfate is between 15,000 and 40,000. Hyaluronic acid is an acidic glycosaminoglycan; the basic building block of hyaluronic acid is an aminodisaccharide which is composed of (beta-1-3)-glycosidically bonded D-glucuronic acid and N-acetyl-D-glucosamine (beta 1-4)-glycosidically bonded to the next unit. Unlike many other glycosaminoglycans, hyaluronic acid does not carry any sulfate groups and is not protein-bound in the tissue.

Collagen consists of protein fibers and occurs in human skin in three different types (type I, III and IV). In collagen, the individual polypeptide chains, which each contain many of the amino acid proline and glycine as every third residue, are wound around one another to form a triple helix. The collagen fibers are synthesized in the fibroblasts as tropocollagen and passed into the extracellular matrix. The stimulation according to the invention of the synthesis of collagen leads to an increase in the production of collagen and thus to increased intermolecular strength of the dermis and thereby to skin which appears more taut. Elastin is likewise a fibrous protein. It consists of unstructured covalently crosslinked polypeptide chains which form a rubber-like elastic material. After being synthesized in the skin cells, elastin is passed into the extracellular matrix. The stimulation according to the invention of the synthesis of elastin polypeptide chains leads to an increase in the production of elastin and thus to an increase in the elasticity of the skin.

Fibronectin represents a group of high molecular weight glycoproteins (MR of the dimer about 440,000 to 550,000) which are found in the extracellular matrix and in extracellular fluids. The fibronectin dimer, an elongate molecule of dimensions 600×25 A, which is bonded by two disulfide bridges, binds, by linear combination of three different repeating domains, inter alia collagens, glycosaminoglycans, proteoglycans, fibrin(ogen), deoxyribonucleic acids, immunoglobulins, plasminogen, plasminogen activator, thrombospondin, cells and microorganisms. Through these properties it mediates, for example, the adhesion of connective tissue cells to collagen fibrils or of thrombocytes and fibroblasts to fibrin (contribution to wound healing).

The proteoglycans, like the glycoproteins, consist of carbohydrates and proteins, but the proportion of polysaccharides is greater in the proteoglycans. The proteoglycans of the skin contain dermatan sulfate. About 140 such proteoglycans are attached non-covalently by means of smaller proteins (link proteins) to a hyaluronic acid chain to form molecule aggregates having a mean molar mass of about 2 million. The polyanionic aggregates, which are distinguished by their water-binding capacity, can form solid gels which impart elasticity and tensile strength to the supporting tissue (extracellular matrix). In mucosa, they protect the epithelia. The stimulation according to the invention of the synthesis of proteoglycans and hyaluronic acid leads to a greater amount of extracellular matrix and thus to increased elasticity and tensile strength.

Glycation is a non-enzymatic reaction of glucose or other sugars with proteins to form glycoproteins. This reaction leads to unintentional changes in the collagen and elastin and thus to changes in the extracellular matrix. The function of the collagen and the extracellular matrix is disrupted. The prevention according to the invention of glycation leads to a reduction in the non-enzymatic change in collagen and elastin and thus to the prevention of a reduced function of the extracellular matrix.

EXAMPLES

Examples 1 to 6, Comparative Examples C1 and C2

Effectiveness Against Skin Ageing

Background:

The enzyme glucose-6-phosphate dehydrogenase (G6PDH) catalyzes the first step of the so-called "pentose pathway", in which an important DNA component, namely deoxyribose, is formed. Glucose 6-phosphate (G6P) is thereby converted into 6-phosphogluconate (6PG) by means of G6PDH. At the same time, the coenzyme NADP required thereby is reduced to NADPH2, which in turn is able to catalyze a large number of other biological reactions such as, for example, the recycling of glutathione or lipid synthesis. Reduced glutathione protects many enzymes which have SH groups and cells against oxidative stress, such as, for example, the action of UV. The G6PDH content is thus an important parameter for cell protection and skin renewal.

Method:

G6PDH activity was determined in vitro on human fibroblasts by the enzymatic method of Okada, while the DNA content was determined by the Desaulniers method. The results are summarized in Table 1. The results of 3 series of measurements with triple determination are given in %-rel. compared to a blank sample.

TABLE 1

Stimulation of G6PDH activity (in %-rel.)

| | | DNA | | G6PDH | |
|---|---|---|---|---|---|
| Substance | Conc. % w/v | after 3 d | after 6 d | after 3 d | after 6 d |
| Blank sample | 0 | 100 | 100 | 100 | 100 |
| C1 Uvinul A | 0.001 | 97 | 93 | 88 | 81 |
| C2 Octocrinyl | 0.001 | 95 | 90 | 89 | 85 |
| 1 L-Carnosine | 0.001 | 111 | 120 | 105 | 109 |
| 2 Carnicine*HCl | 0.001 | 106 | 118 | 104 | 109 |
| 3 L-Carnosine + Uvinul A (1:1) | 0.001 | 119 | 137 | 115 | 120 |
| 4 L-Carnosine + Octocrinyl (1:1) | 0.001 | 120 | 141 | 116 | 125 |
| 5 L-Carnosine + Uvasorb HEB (1:5) | 0.001 | 122 | 138 | 114 | 121 |
| 6 L-Carnosine + NeoHeliopan (1:5) | 0.001 | 125 | 140 | 110 | 112 |

As is shown by the examples, the administration of carnosines has the result that both the amount of cellular DNA and G6PDH increases in a statistically significant manner. This effect, which was already unexpected, can be further increased by combination with UV sun protection filters, although these show no effect at all on their own.

Examples 7 and 8

Inhibition of Apoptosis Induction

Background:

Apoptosis, unlike necrosis, is the natural purposive cell death of specific undesired or damaged cells. It is an active process of the cells (suicide on command). In the case of skin ageing especially, a deficiency of growth factors in the skin leads to induced apoptosis of the skin cells. In the cells affected by apoptosis, the nuclear DNA is degraded by the specific enzyme endonuclease and the DNA fragments are passed into the cytoplasm.

Method:

The ability of carnosines to prevent apoptosis induced by a deficiency of growth factors in human skin cells was studied. These tests were carried out in vitro on human fibroblasts and human keratinocytes. The human cells were cultivated in a nutrient medium (DMEM=Dulbecco minimum essential medium from Life Technologie Sarl) with 10% fetal calf serum (from Dutcher). Bromodeoxyuridine (BrdU) was added to the nutrient medium; it was incorporated into the DNA and later served for detection of the DNA fragments in the cytoplasm. After an incubation period of two days, the nutrient medium was replaced by nutrient medium (DMEM) without fetal calf serum. The active substance to be tested was added. For comparison, a cell sample without active substance to be tested was incubated. After a further incubation period of one or two days at 37° C., the cells were recovered by trypsinization according to the method of Dunnebacke and Zitcer described in: Cell and tissue culture, Ed.: J. Paul, Churchill Livingstone, 1975, p. 226. After the trypsinization, the cells were centrifuged and counted. Then the content of BrdU in the DNA fragments from the cytoplasm was determined by means of the ELISA test (ELISA kit from Roche). The content of BrdU is a measure of the DNA fragments which have passed from the nucleus, the cell core, into the cytoplasm. The results were based on a million cells and given in percent in comparison to the control. The results are summarized in Table 2 below.

TABLE 2

Number of cells and content of DNA fragments

| | Substance | Conc. [% w/v] | Cell count | Content of DNA fragments |
|---|---|---|---|---|
| | Control | 0 | 100 | 100 |
| 7 | L-Carnosine | 0.001 | 129 | 85 |
| 8 | Carnicine*HCl | 0.001 | 118 | 88 |

The in vitro examples show that, by using carnosines, apoptosis in human cell cultures and the content of free DNA fragments in the cytoplasm, and thus the degree of damaged DNA in the nucleus, fall.

Examples 9 and 10

Stimulation of the Synthesis of Dermal Macromolecules (GAG)

Background:

The aim of these tests is to demonstrate a stimulating activity of carnosines on the synthesis of dermal macromolecules on human fibroblast cultures in vitro. The dermis is composed of cells (fibroblasts and mast cells), tissue components (collagen and elastin) and so-called ground substances. These ground substances include, for example, glycosaminoglycan (GAG), hyaluronic acid, chondroitin sulfate, dermatan sulfate and glycoproteins. As a result of skin ageing, the intermolecular strength and elasticity of the dermis, and thus the tautness of the skin, is reduced. Likewise, the number of skin cells present, in particular fibroblasts, is reduced as the skin ages. The collagen fibers are fragmented over time, and the proportion of insoluble to soluble collagen increases. The fine dermal elastic fibers become coarse and are destroyed. The synthesis of GAG (glycosaminoglycan) is reduced. All these processes contribute to skin ageing and the manifestations thereof, such as wrinkles and lack of tautness of the skin.

Method:

The measuring method is based on staining macromolecules in a culture of human fibroblasts which, with type I collagen, forms a collagen gel or collagen lattice fibers. Certain regions of those fibers are quantified by means of staining reagents for the proportion of the mentioned macromolecules.

For that purpose, a suspension of human fibroblasts was mixed with a solution of type I collagen (1-2 mg/ml). This mixture was incubated in a defined nutrient medium (DMEM=Dulbecco minimum essential medium, Life Technologie Sarl) comprising 0.5 or 2% by weight fetal calf serum (FCS) for 14 days at 37° C. in a 5% $CO_2$ atmosphere in Petri dishes (5 ml per dish) with the addition of different concentrations of the plant extracts to be tested.

The kinetics of the collagen gel concentration was determined 2 to 3 times per week by measuring two perpendicular diameters on each collagen gel using a microscope with an image analysis system. The size of the area is shown in $cm^2$ in Table 8. After incubation for 14 days, the density of the collagen gel was determined by image analysis with a light source of visible light, by comparatively analyzing different gray stages. This is a relative determination of the density (0=clear or white and 1=black), which cannot be given a unit.

After an incubation period of 7 and 14 days, biopsies (tissue samples) were taken and histological sections of the collagen gel containing human fibroblasts were obtained. The synthesis of macromolecules was analyzed and quantified by the staining of glycosaminoglycan with PAS Alcian blue, for example from SIGMA, by the periodic acid-Schiff method (PAS) described in: Mowry R W, Anal. NY Adad. Sci. 106 Art 2, 402, 1963. The stimulation of the synthesis of macromolecules was evaluated in the immediate vicinity of fibroblasts. This zone is also referred to as the "perifibroblast area".

The "perifibroblast" secretion, or the secretion of fibroblasts into the periphery, was quantified by an image analyzer by means of a microscope. Reactive structures in the "perifibroblast area" were detected, and the different gray stages were comparatively determined. The values of the gray stages were thereby subdivided from 0=white to 255=black. These parameters are directly proportional to the intensity of the synthesis of macromolecules and thus to the GAG content of the fibroblasts.

The results of the values of these parameters are shown in Table 3 below and are to be regarded directly as representative values for the synthesis activity of the fibroblasts. The content of GAGs is described as a relative value of the gray stage.

TABLE 3

Content of GAGs in tissue samples of human fibroblasts containing collagen

| | Substance | Area [cm2] | | Density | GAG content | |
| --- | --- | --- | --- | --- | --- | --- |
| | | 7 days | 14 days | 14 days | 7 days | 14 days |
| | Control* | 7.6 | 4.4 | 0.35 | 12.0 | 10.1 |
| 9 | 0.5% by weight FCS + 0.01% by weight L-carnosine | 10.1 | 6.0 | 0.25 | 12.1 | 15.1 |
| 10 | 0.5% by weight FCS + 0.01% by weight carnicine*HCl | 9.9 | 5.8 | 0.25 | 11.8 | 13.3 |

*5% by weight fetal calf serum (FCS)

The results of the determination of the glycosaminoglycan content in tissue samples of collagen gel containing fibroblasts, especially in the perifibroblast area, show a significant increase in the GAG content as compared with the standard after an incubation period of 14 days with the addition of carnosines. This indicates, in vitro, a regenerating and revitalizing activity of carnosines on human fibroblasts.

Examples 11 and 12

Inhibition of Elastase Activity

Background:

Elastase is a protease which is secreted by the fibroblasts under inflammatory conditions and is jointly responsible for the degradation of dermal macromolecules, such as, for example, collagen and elastin, and thus for skin ageing.

Method:

In order to determine the effectiveness of the plant extract in inhibiting the release of elastase, pancreas elastase (a serine protease) was studied and, as substrate, elastin was labeled with a chromogenic synthetic substrate. The system was incubated with the active ingredients for 30 minutes at room temperature and then, after centrifugation, the optical density of the dye at 410 nm was determined. The amount of extracts used was 0.3% by weight. The results are summarized in Table 4. The results were given relative to a control as standard (=0%); al-antitrypsin was used as the standard.

TABLE 4

Elastase inhibition

| | Substance | Inhibition [%] |
| --- | --- | --- |
| 11 | L-Carnosine | 32 |
| 12 | Carnicine*HCl | 28 |

The results show that carnosines are capable of inhibiting elastase and especially pancreas elastase.

Examples 13 and 14

Inhibition of the Glycation of Collagen

In order to demonstrate that carnosines inhibit the non-enzymatic glycation of macromolecules, type I collagen was treated with glucose and the extracts for a period of 21 days at 45° C. The suspensions were then centrifuged and the content of Schiff's bases in the supernatant liquid was determined by fluorescence measurement at 430 nm. The results are summarized in Table 5. The results are again based on the control as standards (without extract and without glucose).

TABLE 5

Inhibition of the glycation of collagen

| | Substance | Inhibition [%] |
|---|---|---|
| | Control without glucose | 46 |
| | Control with glucose | 100 |
| 13 | L-Carnosine | 68 |
| 14 | Carnicine*HCl | 65 |

The in vitro results indicate that carnosines are capable of inhibiting the glycation of collagen and thus of slowing the ageing process of the dermis by glycation of collagen fibers.

In Table 6 below, a total of 10 exemplary formulations are given.

TABLE 6

Skin care agents

| Composition | A | B | C | D | E | F | G | H | I | J |
|---|---|---|---|---|---|---|---|---|---|---|
| Polyglyceryl-2 dipolyhydroxystearate | 4.0 | 3.0 | — | 5.0 | — | — | — | — | — | — |
| Polyglyceryl-3 diisostearate | 2.0 | 1.0 | — | — | — | — | — | — | — | — |
| Cetearyl glucoside (and) cetearyl alcohol | — | — | — | — | 4.0 | — | — | — | 3.0 | — |
| Ceteareth-20 | — | — | — | — | — | — | — | 2.0 | — | — |
| Polyglyceryl-3 methylglucose distearate | — | — | 3.0 | — | — | — | 4.0 | — | — | — |
| Polyglyceryl-2 dipolyhydroxystearate (and) Lauryl glucoside (and) glycerol | — | — | — | — | — | 3.5 | — | — | 2.5 | — |
| Beeswax | 3.0 | 2.0 | 5.0 | 2.0 | — | — | — | — | — | — |
| Glyceryl stearate | — | — | — | — | — | 2.0 | — | — | — | 4.0 |
| Cetearyl alcohol | — | — | 2.0 | — | 2.0 | 4.0 | 2.0 | 4.0 | 4.0 | 1.0 |
| PVP/hexadecene copolymer | — | — | — | — | — | 3.0 | — | — | — | 2.0 |
| Cocoglycerides | 5.0 | — | 10.0 | — | 8.0 | 6.0 | — | — | 5.0 | 5.0 |
| C12/15 alkyl benzoate | — | 6.0 | — | 2.0 | — | — | — | — | — | 2.0 |
| Oleyl erucate | 7.0 | 4.0 | 3.0 | 5.0 | 4.0 | 3.0 | — | — | 5.0 | 4.0 |
| Dicaprylyl ether | 3.0 | — | 6.0 | 8.0 | 6.0 | 5.0 | — | — | 4.0 | 6.0 |
| Mineral oil | — | 4.0 | — | 4.0 | — | 2.0 | — | — | — | — |
| Hexadecanol (and) hexyldecyl laurate | — | 7.0 | 3.0 | 7.0 | 4.0 | — | — | — | 1.0 | — |
| Panthenol/bisabolol | 1.2 | 1.2 | 1.2 | 1.2 | 1.2 | 1.2 | 1.2 | 1.2 | 1.2 | 1.2 |
| L-Carnosine | 1.0 | 1.0 | 1.0 | 1.0 | 1.0 | 1.0 | 1.0 | 1.0 | 1.0 | 1.0 |
| Tocopherol/tocopheyl acetate | 0.5 | 1.0 | 1.0 | 2.0 | 1.0 | 1.0 | 1.0 | 2.0 | 0.5 | 2.0 |
| Sodium phenylbenzimidazole sulfonate | 3.0 | — | — | 3.0 | — | — | 2.0 | — | 2.0 | — |
| Octocrylene | — | 5.0 | — | — | — | 4.0 | 5.0 | — | — | 10.0 |
| Benzophenone-3 | 1.5 | — | — | 2.0 | 1.5 | — | — | — | 2.0 | — |
| Isoamyl p-methoxydnnamate | 5.0 | — | 4.0 | — | 2.0 | 2.0 | 4.0 | 10.0 | — | — |
| Octyl methoxycinnamate | 4.0 | — | 4.0 | 3.0 | 2.0 | 3.0 | 4.0 | — | 10.0 | 2.0 |
| Octyl triazone | 2.0 | 4.0 | 3.0 | 1.0 | 1.0 | 1.0 | 4.0 | 3.0 | 3.0 | 3.0 |
| Zinc oxide | — | 6.0 | 6.0 | — | 4.0 | — | — | — | — | 5.0 |
| Titanium dioxide | — | — | — | — | — | — | — | 5.0 | — | — |
| Glycerol (86% strength) | 5.0 | 5.0 | 5.0 | 5.0 | 5.0 | 5.0 | 5.0 | 5.0 | 5.0 | 5.0 |

(A) W/O day creams;
(B-D) W/O skincare lotions;
(E-G) O/W skincare lotions;
(H-J) O/W skincare creams

The invention claimed is:

1. A method of inhibiting elastin degradation in human skin not caused by the influence of light, comprising
topically applying a preparation consisting of:
a compound selected from the group consisting of carnosine, L-carnosine, D-carnosine; and
at least one carrier;
wherein the carnosine, L-carnosine, or D-carnosine is included in the preparation in an amount effective to inhibit activity of elastase.

2. The method of claim 1, wherein the preparation is applied once to twice daily over a period of from 7 to 14 days.

3. The method of claim 1, wherein the carrier is selected from the group consisting of water, alcohols, esters, butylene glycol, dipropylene glycol, ethanol, ethoxydiglycol, ethyl acetate, glycerol, propanol, isopropanol, macrogols, propylpropylene glycol(2) methyl ether, propylpropylene glycol (3) methyl ether, propylene carbonate, propylene glycol, triethylene glycol, isoparaffin, amyl acetate, amyl benzoate, benzyl acetate, butyl acetate, butylene glycol, butyl lactate, butooctyl benzoate, butooctyl salicylate, C10-C13 alkanes, C14-C17 alkanes, C11-C15 cycloalkanes, caprylyl butyrate, isoparaffins, diacetin, triacetin, dicaprylyl ether, dicaprylyl maleate and mixtures thereof.

4. The method of claim 1, wherein pancreas elastase activity is inhibited.

5. A method of inhibiting elastin degradation in human skin not caused by the influence of light, comprising
topically applying a preparation consisting of:
(a) at least one compound selected from the group consisting of carnosine, L-carnosine, D-carnosine, and
(b) at least one UV sun protection factor, preferably at least one UV-A and at least one UV-B sun protection factor, and optionally
(c1) a carrier,
(c2) an oily substance, and/or
(c3) an emulsifier,
is applied topically in an amount effective to inhibit release of the elastase.

6. The method as claimed in claim 5, wherein the preparation is applied once to twice daily over a period of from 7 to 14 days.

7. The method of claim 5, wherein the UV sun protection filter is consisting of UV-A filters, UV-B filters and sun protection pigments and mixtures thereof.

8. The method of claim 7, wherein the UV-A filters are selected from the group consisting of benzoyl methane and enamine compounds and mixtures thereof.

9. The method of claim 7, wherein the UV-B filters are selected from the group consisting of 3-benzylidene camphor and 3-benzylidene norcamphor and derivatives thereof, 4-aminobenzoic acid derivatives, esters of cinnamic acid, esters of salicylic acid, derivatives of benzophenone, esters of benzalmalonic acid, triazine derivatives, propane-1,3-diones, ketotricyclo-(5.2.1.0)decane derivatives, 2-phenyl-benzimidazole-5-sulfonic acid and salts thereof; sulfonic acid derivatives of benzophenones, sulfonic acid derivatives of 3-benzylidene camphor and mixtures thereof.

10. The method of claim 7, wherein the sun protection pigments are selected from the group consisting of zinc oxide, titanium dioxide, iron oxide(s), zirconium oxide, silicon dioxide, manganese oxide, aluminum oxide, cerium oxide, silicates, barium sulfate and zinc stearate and mixtures thereof.

11. The method of claim 5, wherein the carrier is selected from the group consisting of water, alcohols, esters, butylene glycol, dipropylene glycol, ethanol, ethoxydiglycol, ethyl acetate, glycerol, propanol, isopropanol, macrogols, propylpropylene glycol(2) methyl ether, propylpropylene glycol (3) methyl ether, propylene carbonate, propylene glycol, triethylene glycol, isoparaffin, amyl acetate, amyl benzoate, benzyl acetate, butyl acetate, butylene glycol, butyl lactate, butooctyl benzoate, butooctyl salicylate, C10-C13 alkanes, C14-C17 alkanes, C11-C15 cycloalkanes, caprylyl butyrate, isoparaffins, diacetin, triacetin, dicaprylyl ether, dicaprylyl maleate and mixtures thereof.

12. The method of claim 5, wherein pancreas elastase activity is inhibited.

* * * * *